(12) United States Patent
Bürgi et al.

(10) Patent No.: US 10,945,849 B2
(45) Date of Patent: Mar. 16, 2021

(54) JOINT SOCKET IMPLANT

(71) Applicant: JOSSI HOLDING AG, Islikon (CH)

(72) Inventors: Pascal Bürgi, Volketswil (CH);
Christian Gugler, Frauenfeld (CH);
Daniel Nadler, Hettlingen (CH)

(73) Assignee: JOSSI HOLDING AG, Islikon (CH)

( * ) Notice: Subject to any disclaimer, the term of this patent is extended or adjusted under 35 U.S.C. 154(b) by 154 days.

(21) Appl. No.: 15/776,492

(22) PCT Filed: Nov. 22, 2016

(86) PCT No.: PCT/EP2016/078390
§ 371 (c)(1),
(2) Date: May 16, 2018

(87) PCT Pub. No.: WO2017/089332
PCT Pub. Date: Jun. 1, 2017

(65) Prior Publication Data
US 2018/0325678 A1      Nov. 15, 2018

(30) Foreign Application Priority Data

Nov. 23, 2015 (EP) .................................. 15195856

(51) Int. Cl.
*A61F 2/34* (2006.01)
*A61F 2/30* (2006.01)

(52) U.S. Cl.
CPC .......... *A61F 2/34* (2013.01); *A61F 2002/305* (2013.01); *A61F 2002/30332* (2013.01); *A61F 2002/30367* (2013.01); *A61F 2002/30485* (2013.01)

(58) Field of Classification Search
USPC ............................................. 623/22.21–22.39
See application file for complete search history.

(56) References Cited

U.S. PATENT DOCUMENTS

| | | | |
|---|---|---|---|
| 5,092,897 A * | 3/1992 | Forte | ..................... A61F 2/4637 623/22.18 |
| 5,800,555 A | 9/1998 | Gray, III | |

FOREIGN PATENT DOCUMENTS

| | | |
|---|---|---|
| EP | 0 663 193 A1 | 7/1995 |
| EP | 1 297 800 A2 | 4/2003 |
| FR | 2 936 145 A1 | 3/2010 |
| WO | 02/064066 A2 | 8/2002 |

OTHER PUBLICATIONS

European Search Report Corresponding to 15195856.8 dated May 17, 2016.
International Search Report Corresponding to PCT/EP2016/078390 dated Feb. 16, 2017.
Written Opinion Corresponding to PCT/EP2016/078390 dated Feb. 16, 2017.

* cited by examiner

*Primary Examiner* — Yashita Sharma
(74) *Attorney, Agent, or Firm* — Davis & Bujold PLLC; Michael J. Bujold

(57) ABSTRACT

An outer shell (1) for a joint socket implant, in particular for an acetabular implant, which comprises a convex outer face (3) and a concave inner face (4) for receiving an inner shell. The concave inner face (4) has at least partially a toothing system (7), in particular a circular circumferential region (6) thereof. Via the toothing system (7), an inhibition of the rotatability of the two shells, relative to one another, can be achieved upon insertion of the inner shell into the outer shell (1).

15 Claims, 5 Drawing Sheets

JOINT SOCKET IMPLANT

The present invention relates to a joint socket implant, in particular an acetabular implant, comprising an outer shell and an inner shell.

When damage occurs to a joint socket of a patient, for example to the acetabulum, it is common practice to implant an artificial joint socket. Such joint sockets are often constructed in two parts, namely an outer shell and an inner shell. The outer shell serves to embed the joint socket in the bone. The inner shell, which is inserted into the outer shell, forms a bearing surface for a corresponding joint head. While outer shells are often produced from a metal, the materials customarily used for inner shells are ceramic materials and also plastics, in particular polyethylene, but also suitable metals.

In the case of ceramic inner shells, and also in the case of inner shells made from plastic or metal, it is essential that a rotation with respect to the outer shell is prevented. This is because the joint shell can quickly suffer damage if friction occurs between parts inside the joint shell that are not provided for this purpose. Abraded particles can also end up on the bearing surfaces of the joint and cause rapid wear there or, in the worst case, can even migrate into the patient's body and cause damage. Moreover, particularly in the case of inner shells that are higher on one side, it is necessary to ensure that they are fixed in a defined angle position.

Ceramic or metallic inner shells are generally of conical configuration, as a result of which, after insertion into an outer shell, they are able to apply a sufficiently high retaining force against the torque transmitted by a joint head. By contrast, inner shells made of a plastic material have to be additionally secured against rotation. Many outer shells therefore have anti-rotation means in their edge region in the form of cuttings, or scallops, in which convex structures of the inner shell engage. However, the production of such joint sockets is complex and costly.

Therefore, in recent times, outer shells have been developed that have, on their concave inner face, barb-shaped penetration elements which bore their way into an inserted inner shell made of plastic and thereby secure the inner shell against rotation. For example, EP 0 663 193 B1 discloses a revision socket for an artificial hip joint. Said socket comprises a hemispherical support shell and a correspondingly dimensioned inner shell. The concave inner face of the support shell is provided with penetration elements which, upon insertion of the inner shell, penetrate into the outer face thereof in order to prevent rotation. In addition, U.S. Pat. No. 5,800,555 discloses a bearing component for a ball-and-socket joint prosthesis. This bearing component is inserted into an outer shell which, on its inner face, has protrusions for securing against rotation. For this purpose, the protrusions penetrate into the outer surface of the bearing component.

Anti-rotation means of this kind have the advantage that their implementation does not require any structural measures to be carried out on the inner shell. However, considerable costs are involved in forming the penetration elements during the production of the outer shell. It is often not possible for the penetration elements to be produced in one piece with the shell, which necessitates the formation of drilled holes and the fitting and pressing-in of the elements. If the penetration elements are made of a different material than the outer shell, this has to be declared in the product authorization, which makes the latter more difficult. To permit insertion of the inner shell into the outer shell, spike-shaped penetration elements also have to be arranged at the bottom of the outer shell, as a result of which they are located relatively close to the longitudinal central axis of the outer shell and can thus transmit only a low torque to the inner shell.

Moreover, WO 02/064066 A2 has disclosed an implantable socket for hip-joint endoprostheses, in which the bearing shell can be inserted in any desired rotational position into the inner receiver of the socket and is fixed securely against rotation. For this purpose, a circular multiple toothing system is provided on the inner circumference of the receiver and engages in the bearing shell in order to prevent rotation.

A similar solution is described in FR 2 936 145, where individual teeth are each arranged in pairs on a circumferential region.

A disadvantage of the previously known inhibition of rotation by a toothing system is that high pressing-in forces are needed in order to insert the inner shell, and there is the danger of the material of the inner shell being damaged, wherein undesired chipping takes place and particles of the inner shell may possibly be abraded. The teeth have an unfavorable configuration or they are oversized or too numerous in order to resist a predefined setpoint torque between the two shells parts. Something else that has to be considered is that the pressing-in force required to insert the inner shell is limited if the surgeon has to drive in or press in the inner shell in situ.

It is therefore an object of the present invention to overcome the abovementioned disadvantages of the prior art. In particular, it is an object of the invention to make available a joint socket implant having an anti-rotation means that is as reliable as possible and that is of a simple design. An anti-rotation means of this kind is intended to be easily implementable in existing implant systems. Moreover, its implementation is to be cost-effective and is intended to allow the surgeon easy handling of the implant and stepless axial adjustment with respect to the shell axis.

It is furthermore an object of the present invention to configure the toothing system in such a way that the softer material of the inner shell is not damaged, and in such a way that a maximum torque is able to be transmitted at the lowest possible pressing-in force.

These objects are achieved by a joint socket implant with the features of claim 1. This joint socket implant comprises an outer shell with a convex outer face and a concave inner face, the latter having a toothing system in a circular circumferential region. The flanks of the toothing system are oriented parallel to the longitudinal central axis of the outer shell, and the tooth profile has a tooth height defined as the difference between the radius of the tip circle and the radius of the root circle of the toothing system. The joint socket implant further comprises an inner shell inserted into the outer shell, wherein the hardness of the outer shell is greater than that of the inner shell, and wherein the region of the inner shell coming into contact with the toothing system has an oversize relative to the tip circle of the toothing system. In this way, an inhibition of the rotatability of the two shells relative to each other can be achieved by the material of the inner shell being displaced by the toothing system.

It is particularly advantageous if the toothing system extends continuously, preferably with uniform pitch, about the circular circumferential region on the outer shell. Here, uniform pitch is understood as a constant distance between the individual teeth, specifically such that the toothing system corresponds to an inner toothing extending through 360°.

Advantageously, the outer shell and the inner shell have corresponding axial locking elements, at which they are locked onto each other relative to the common longitudinal central axis. A locking arrangement of this kind is necessary since, with an inner shell made of plastic material, it is not possible to obtain self-locking in the axial direction, for example by a cone connection.

Particularly advantageously, the circumferential region with the toothing system is arranged in a cylindrical portion of the concave inner face of the outer shell adjacent to the corresponding locking elements, relative to the common longitudinal central axis. By the immediate proximity of the locking elements to the toothing system, advantages in terms of production technology can be achieved. With respect to the common longitudinal central axis, it is unimportant whether the toothing system is arranged first, or the locking elements are arranged first, as seen in the direction from the equator of the shell to the pole. It would also be possible in principle to arrange the toothing system and the locking elements in the outer shell at a distance from each other with respect to the common longitudinal central axis. However, it is particularly advantageous if the circumferential region with the toothing system lies closer to the equator of the outer shell than to the pole, with respect to the longitudinal central axis. In this region near the equator, the internal diameter of the outer shell is at its greatest, as a result of which a maximum diameter of the toothing system can also be achieved. In this way, the number of teeth can be increased, and the distance of the teeth from the rotation axis can also be increased, and the greatest possible torque can thus be transmitted.

Moreover, it is particularly advantageous if the toothing system has a width of between 0.5 mm and 5 mm, preferably of between 0.8 mm and 1.6 mm, with respect to the central longitudinal axis. With the width of the toothing system, it is possible to determine the transmissible torque as a function of the penetration depth into the inner shell. The wider the toothing system and therefore the greater the maximum possible engagement relative to the longitudinal central axis, the higher the torque that can be transmitted at the toothing system.

Moreover, it is particularly advantageous if the toothing system penetrates into the material of the inner shell with a tooth penetration depth of between 0.1 and 1.0 mm, preferably of between 0.15 mm and 0.3 mm. It has surprisingly been found that the pressing-in force is determined substantially by the tooth penetration depth and only inappreciably by the aforementioned tooth width. The greater the penetration depth and the more teeth the toothing system has, the greater the required pressing-in force. However, the penetration depth ought to be as small as possible in order to ensure that there is no damage or chipping of the material of the inner shell. It follows from this that the number of teeth should be as high as possible and that their penetration depth should be kept as small as possible in order to ensure that the pressing-in force can be kept low. The transmissible torque can accordingly be defined with the aid of the tooth width.

It has proven particularly advantageous if the total number of teeth of the toothing system and the width of the teeth relative to the longitudinal central axis are chosen in such a way that the inhibition of the rotatability always exceeds a predefined setpoint torque. The lowest transmissible torque is predefined by the relevant medical standards and has to be complied with in each case. At a predefined penetration depth of between 0.1 mm and 1 mm, and depending on the shell size or the diameter of the toothing system, it is thus possible to optimize the number of teeth and their width.

The individual teeth of the toothing system can enclose an angle of preferably 45° to 100°. For reasons relating to production technology, a slight flattening or rounding will always be present at the top. An angle of more than 100° leads to correspondingly wide teeth at the tooth root, thereby reducing the total number of teeth that can be accommodated on the circumferential region.

It has also proven particularly advantageous if the side flanks of the teeth are configured as plane surfaces. This ensures that as far as possible the entire tooth flank bears on the inner shell.

Further advantages can be achieved if a hollow space remains between the side flanks of adjacent teeth and the inner shell inserted into the toothing system. In the case of inner shells made of soft material, this permits a further expansion, in particular a material flow into the hollow space under loading. It is in this way possible to avoid harmful material stresses which lead to an increased pressing-in force or an undesired expansion of the material toward the longitudinal central axis.

In certain cases, it is also possible that the toothing system extends only partially about the circular circumferential region. A partial interrupted toothing system of this kind has the advantage that the pressing-in force can be reduced, specifically while the penetration depth remains the same.

Particularly advantageously, the inner shell is made of a plastic material, in particular of a polyethylene, with a Shore hardness D of between 50 and 85. A plastic material with this hardness has optimal material properties, such that the inner shell can be pressed into the toothing system without being destroyed.

Preferably, a torque of more than 10 Nm (Newton meter), preferably of more than 12 Nm, can be transmitted by means of the toothing system. This is the afore-mentioned setpoint torque, which is predefined by the relevant medical standards, for example by the "Guidance document for testing acetabular cup prostheses" of the US Federal Drug Administration (FDA). The stated values include a safety factor in relation to the torques that actually occur under loading and that can be triggered by a patient.

The outer shell for the joint socket implant, in particular for an acetabular implant, has a convex outer face and a concave inner face for receiving an inner shell. The concave inner face has at least partially a toothing system in what is in particular a circular circumferential region. By means of the toothing system, an inhibition of the rotatability of the two shells relative to each other with respect to the common main axis can be achieved upon insertion of the inner shell into the outer shell.

By arranging a toothing system on the concave inner face of the outer shell, a particularly reliable anti-rotation means is created. The toothing system can be easily applied to the outer shell and can be adapted to the particular requirements.

The toothing system is preferably produced by a cutting method, for example by milling or impact cutting. In certain cases, however, production by a shaping process or by erosion is also conceivable.

The toothing system can extend continuously about the in particular circular circumferential region. In this way, a comparatively high torque can be transmitted from the outer shell to the inner shell. However, a comparatively high pressing-in force is also necessary when inserting the inner shell into the outer shell. Therefore, the toothing system can also extend with interruptions about the in particular circular circumferential region. The pressing-in force required for inserting the inner shell into the outer shell can thereby be reduced, although this is at the expense of the transmissible torque. By means of a suitably adapted ratio between the regions with toothing and the interruptions, the anti-rotation means can be configured such that an acceptable torque is able to be transmitted from the outer shell to the inner shell with a minimal pressing-in force.

The radius of the root circle of the toothing system can amount to at least 50%, preferably at least 60%, more preferably at least 70% of the total radius of the outer shell. The more the radius of the root circle approaches the total radius of the outer shell, the greater is the transmissible torque. The root circle is understood as the circle on which the deepest points of the toothing system lie.

The outer shell can have at least one locking element for axially locking the inner shell in the outer shell. Locking elements of this kind are also referred to in specialist jargon as snap-fit connections. Particularly in the case of joint socket implants with inner shells made of plastic, a snap-fit connection of this kind has the effect that the inner shell, upon insertion into the outer shell, can snap or latch into the latter and is thereby held secure. A combination of such a snap-fit connection and of an anti-rotation means according to the invention makes it possible to anchor an inner shell in the outer shell in such a way that it is secured both against rotation and also against falling out.

The in particular circular circumferential region with the toothing system can then be arranged on an axial locking element of the outer shell. Through the combination of locking element and toothing system, it is possible to create a compact structural element which is arranged on the concave inner face of the outer shell and secures the inner shell simultaneously against rotation and against falling out.

The toothing system can have a tooth profile with a height that has at least 1.5 to 2 times the desired penetration depth. This ratio ensures that the material of the inner shell displaced during the pressing-in procedure finds space and therefore does not lead to an increase of the pressing-in force.

The tooth profile of the toothing system can be triangular or trapezoid and can enclose an angle α of 30° to 120°, preferably of 45° to 110°, more preferably of 60° to 100°. Such geometries can be easily applied to the concave inner face of the outer shell. They have favorable characteristics during the penetration of the toothing system into the outer face of the inner shell. Moreover, a tooth profile of this kind generally prevents a relative rotation movement between the insert and the outer shell in a particularly reliable manner.

The flanks of the toothing system can be oriented parallel to the longitudinal central axis of the outer shell. This configuration has the effect that the region of the inner shell coming into contact with the toothing system can be of a cylindrical shape.

With respect to the axial direction, the toothing system can have a width of 10 mm to 0.1 mm, preferably of 5 mm to 0.5 mm, more preferably of 1.6 mm to 0.8 mm.

The circumferential region with the toothing system can be arranged in a cylindrical portion of the concave inner face of the outer shell adjacent to the conical portion. By arranging a conical portion on the concave inner face of the outer shell, tilting of the inner shell during assembly in the operating theater can be effectively avoided.

Depending on their design, outer shells of this kind are suitable both as first-time replacements for a ball-and-socket joint and also as revision shells.

The present invention relates to a joint socket implant comprising an outer shell of the above-described type and an inner shell that is insertable into the outer shell. The hardness of the outer shell is greater than that of the inner shell. Upon insertion of the inner shell into the outer shell, it is thus possible to achieve an inhibition of the rotatability of the two shells relative to each other, by the material of the inner shell being displaced by the toothing system of the outer shell.

In a joint socket implant of this kind, the outer shell can be produced from titanium or from a titanium-based, steel-based, cobalt-based or zirconium-based alloy. However, the outer shell can also be produced from a ceramic material. These materials are ones that are customary in the production of implants. They are characterized by excellent biocompatibility and permit reliable anchoring of the outer shell in a bone of a patient.

The inner shell can be produced from polyethylene, in particular from a UHMWPE, or UXPE, a PEEK or a PEAK. In the context of the present invention, UHMWPE is understood as a polyethylene of ultra-high molecular weight. The stated materials are customary in the production of bearing surfaces in artificial joints. They are characterized by particularly good slip resistance, a long useful life and are well tolerated by patients.

However, it is also possible that the inner shell is a composite structure consisting of one of the abovementioned plastic materials and a metal or a ceramic material. In such a composite structure, the convex outer face of the inner shell facing the outer shell is produced from a plastic material, while the joint-bearing surface is made of metal or a ceramic material. Such composite structures can be very easily pressed into an outer shell according to the invention and, by comparison with an inner shell made purely of plastic, provide a better sliding and abrasion behavior of the bearing surface.

Further advantages and individual features of the invention will become clear from the following description of an illustrative embodiment and from the schematic drawings, in which.

Figure 1:
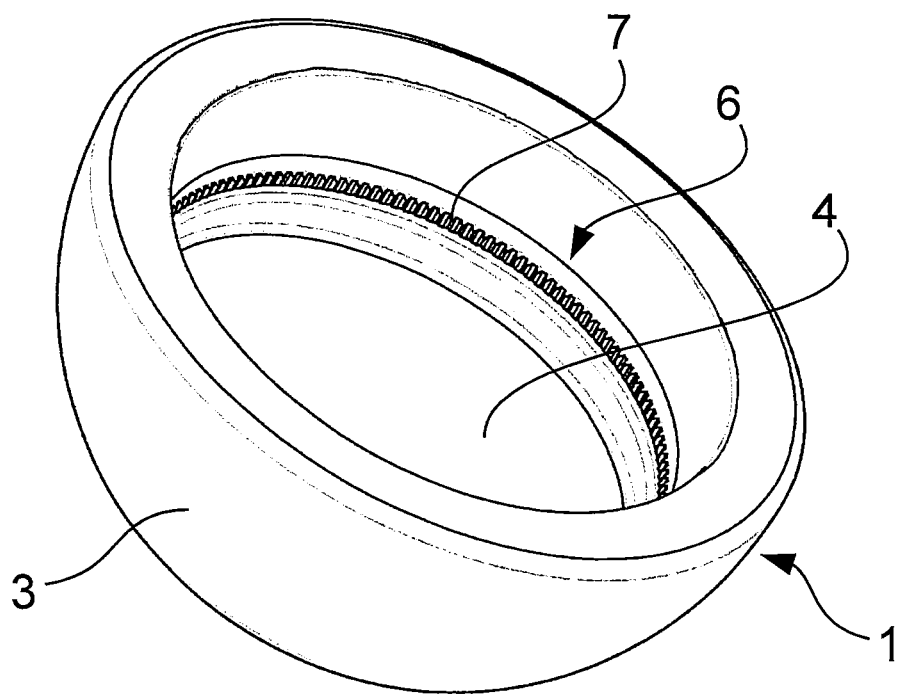
FIG. 1 shows a perspective view of an outer shell for a joint socket implant.

As will be seen from FIG. 1, an outer shell 1 for a joint socket implant 2 (FIG. 9) has a convex outer face 3 and a concave inner face 4. The inner face 4 has a circular circumferential region 6 which is provided with a toothing system 7.

Figure 2:
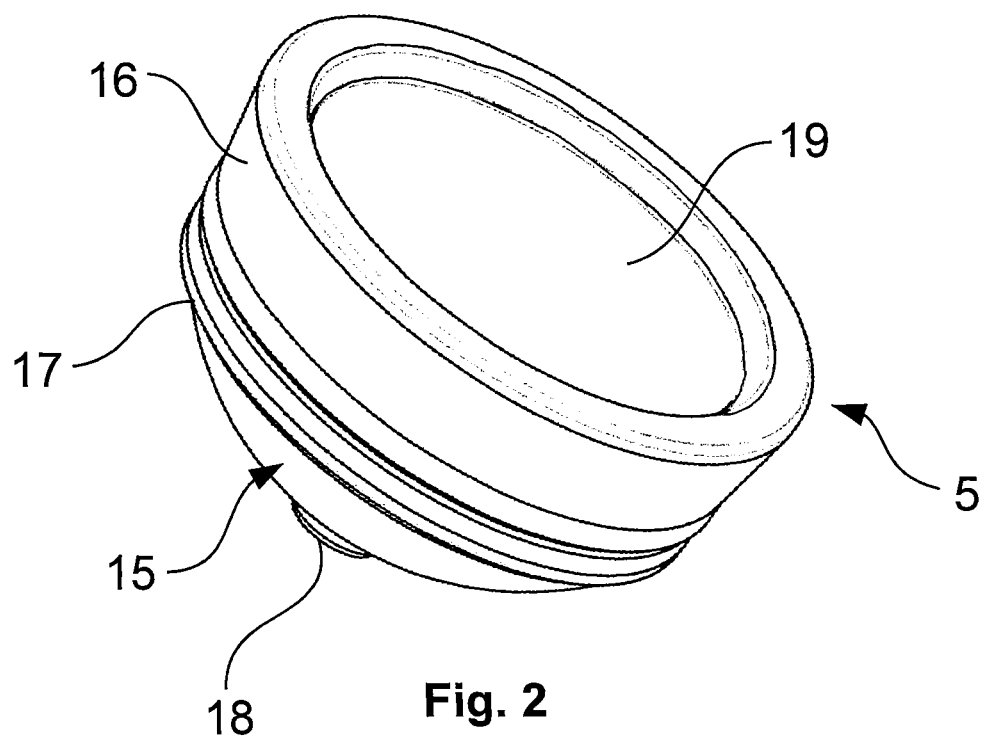
FIG. 2 shows a perspective view of an inner shell for use with an outer shell.

As will be seen from FIG. 2, an inner shell 5 for a joint socket implant 2 according to the invention has, on its concave inner face, a joint-bearing surface 19. The convex outer face 15 is divided into different subregions. Near the equator, the inner shell 5 shown has a conical region 16 and, at the edge region thereof near the pole, a locking element 17 is arranged. A projection 18 is mounted at the pole of the inner shell 5. Both the conical region 16 and the projection 18 serve to prevent tilting of the inner shell 5 in the outer shell 1.

Figure 3:
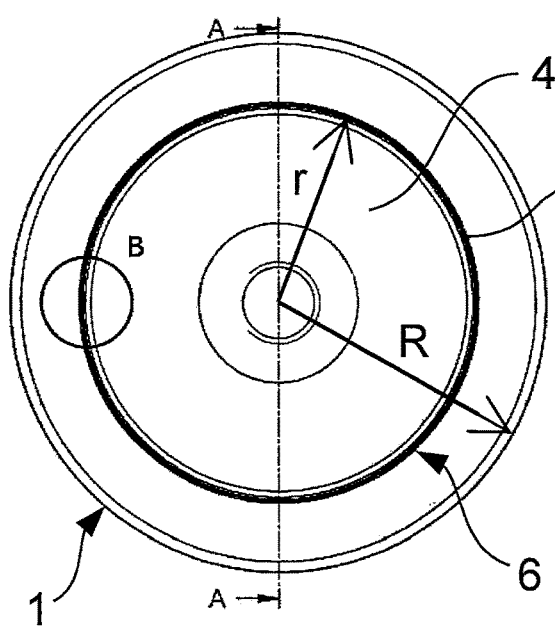
FIG. 3 shows a plan view of an outer shell.

It is clear from FIG. 3 that, in the illustrative embodiment shown, the toothing system 7 is arranged relatively far to the outside on the concave inner face 4 of the outer shell 1. Here, the radius r of the root circle 12 of the toothing system 7 is ca. 70% of the total radius R of the outer shell 1.

Figure 4:
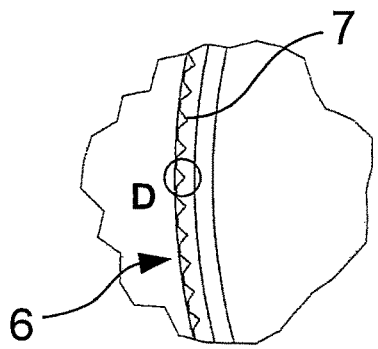
FIG. 4 shows an enlargement of the subregion B according to FIG. 3.

It will be seen from FIG. 4 that a triangular tooth profile is used for the toothing system in the illustrative embodiment under discussion, the triangles being spaced slightly apart from one another.

Figure 5:
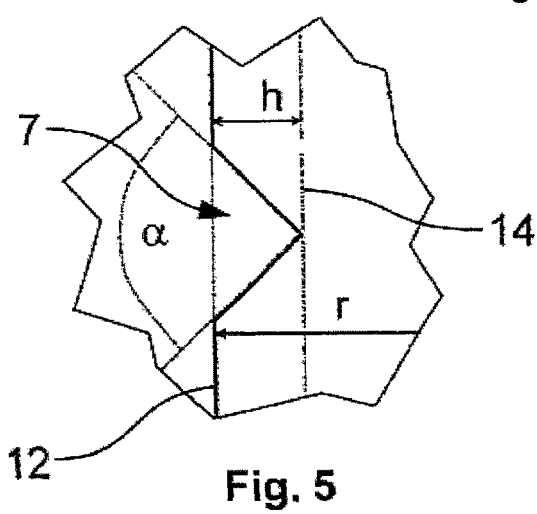
FIG. 5 shows a schematic enlargement of the subregion D according to FIG. 4.

FIG. 5 is a schematic representation of the tooth profile according to FIG. 4. The root circle 12 and the tip circle 14 are plotted with broken lines in the tooth profile. The angle α enclosed by the tooth profile is likewise indicated. It will moreover be seen that the height h of the tooth profile is defined as the difference between the radius of the tip circle 14 and that of the root circle 12.

Figure 6:
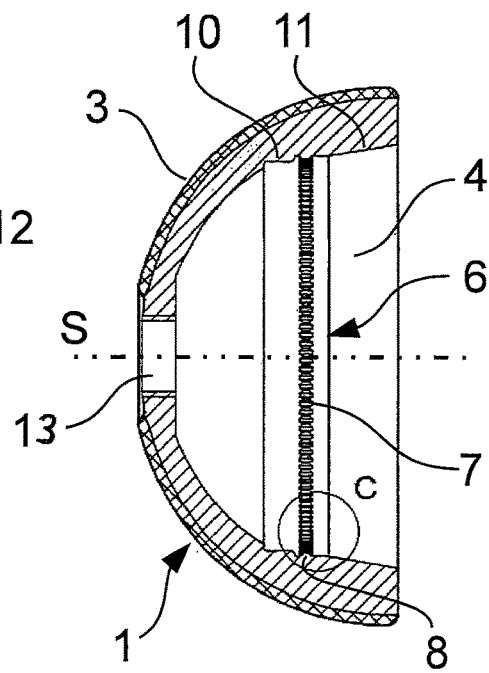
FIG. 6 shows a sectional view of an outer shell through the section plane A according to FIG. 3.

Further details of the outer shell 1 according to the invention will be evident from the sectional view according to FIG. 6. This shows that the concave inner face 4 of the outer shell 1 is divided into different regions. Thus, the region 10, in which the axial locking element 8 equipped with the toothing system 7 is also arranged, has a stepped configuration. By contrast, the region 11 is shaped conically. The outer shell 1 has an opening 13 at its pole. The longitudinal central axis of the outer shell is designated by S.

Figure 7:
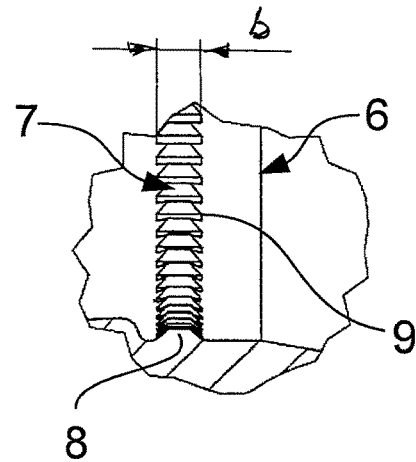
FIG. 7 shows an enlargement of the subregion C according to FIG. 6.

FIG. 7 shows the configuration of the locking element 8 provided with a toothing system 7. It will be seen that the toothing system 7 has the width b which, in the present illustrative embodiment, is identical to that of the locking element. It will moreover be seen that the toothing system 7 here has a trapezoid transverse profile.

Figure 8:
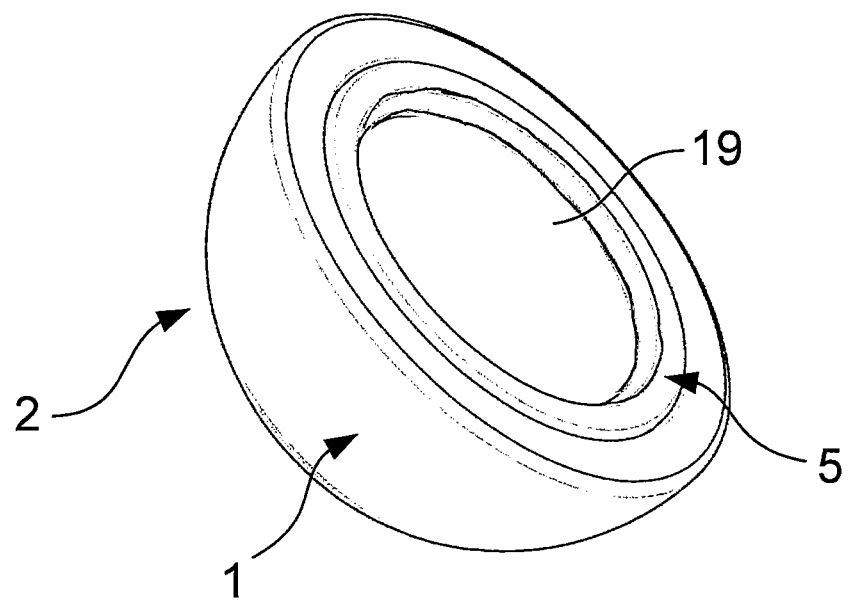
FIG. 8 shows a perspective view of an inner shell inserted into an outer shell.
Figure 9:
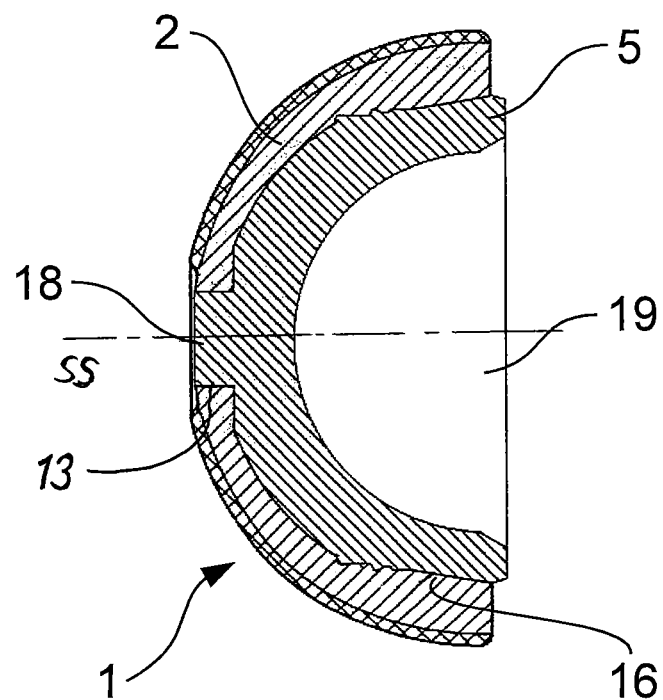
FIG. 9 shows a sectional view of an inner shell inserted into an outer shell.

FIG. 8 shows a perspective view of a joint socket implant 2 according to the invention with outer shell 1 and inner shell 5. The joint-bearing surface 19 on the concave inner face can be seen in particular. FIG. 9 shows a longitudinal section through said joint socket implant 2. It will be seen that the projection 18 at the pole of the inner shell 5 engages in the opening 13 provided for it in the outer shell 1. The common main axis (longitudinal central axis) of outer shell and inner shell is designated by SS.

Figure 10:
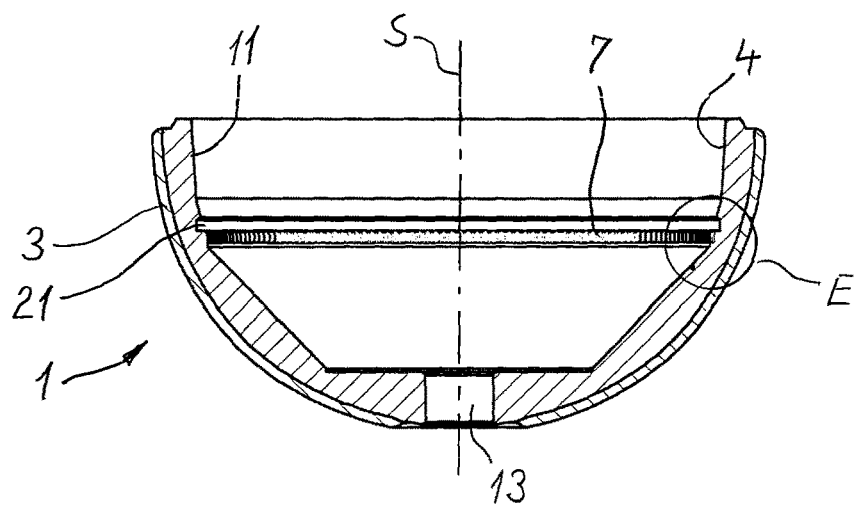
FIG. 10 shows a sectional view of an alternative illustrative embodiment of an outer shell.
Figure 11:
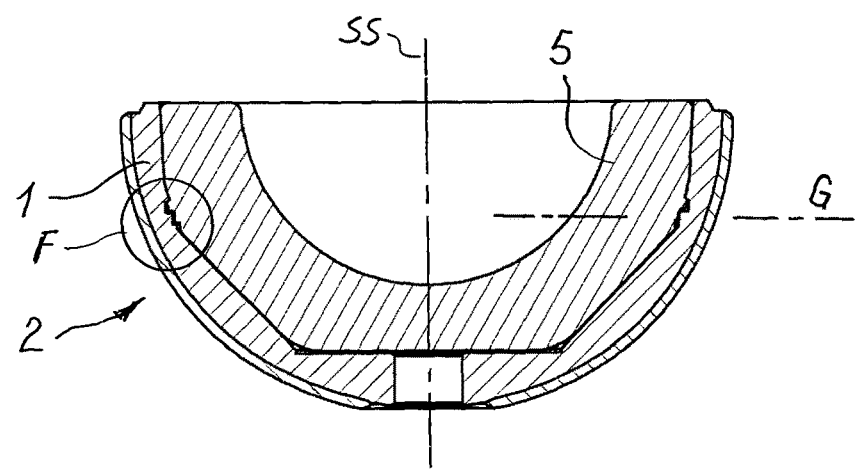
FIG. 11 shows a sectional view of an alternative illustrative embodiment of a joint socket implant using the outer shell according to FIG. 10.
Figure 12:
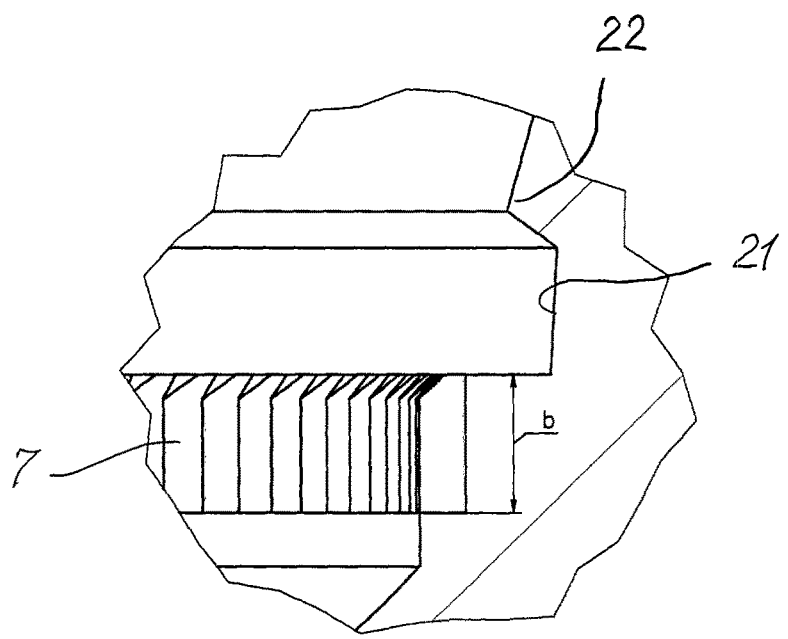
FIG. 12 shows an enlargement of the subregion E according to FIG. 10.
Figure 13:
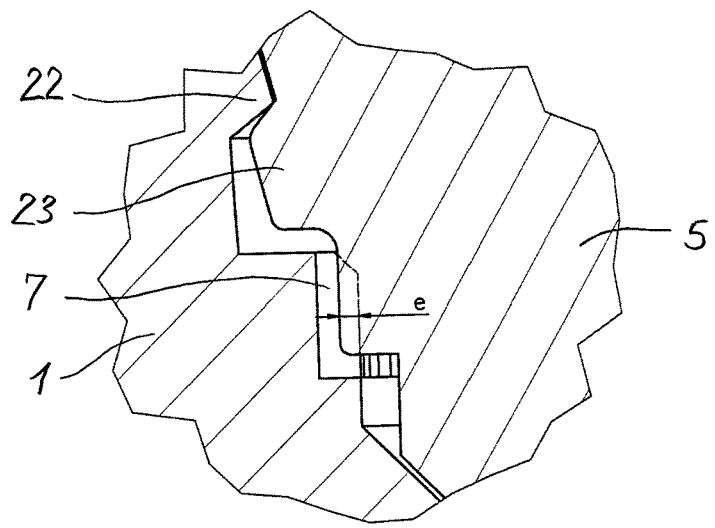
FIG. 13 shows an enlargement of the subregion F according to FIG. 11.
Figure 14:
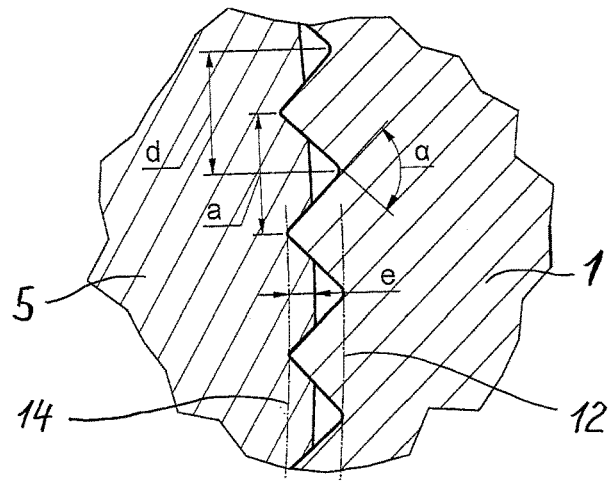
FIG. 14 shows an enlargement of the partial section through the plane G according to FIG. 11.

FIGS. 10 and 11 show a modified illustrative embodiment of a joint socket implant, in which the outer shell has another inner contour. In contrast to the outer shell according to FIG. 6, the toothing system 7 is arranged in another region. The conical inlet region 11 on the inner face 4 is followed by a likewise conical undercut 21, of which the configuration can be seen more exactly in FIG. 12. The shoulder 22 between the undercut 21 and the conical region 11 forms the locking element of the outer shell, behind which locking element a corresponding material shoulder 23 of the inner shell engages with a locking action (FIG. 13). Directly below the undercut 21 is a circumferential cylindrical region at which the toothing system 7 is arranged. The toothing system extends over the width b, hence not over the entire cylindrical region. In contrast to the inner shell according to FIG. 9, the inner shell according to FIG. 11 has no material projection that engages in the opening 13. The situation in the region of the locking connection and of the toothing system can be seen more exactly in FIG. 13. Accordingly, a cylindrical region on the inner shell is oversized in relation to the tip circle of the toothing system, such that, depending on material tolerances, a penetration depth e of the individual teeth into the material of the inner shell 5 is obtained. This penetration depth is shown again in FIG. 14, where the tooth flanks enclose between them an angle α of 90°. The flank angle determines the tooth thickness d in the region of the root circle 12, and the distance between two teeth in the region of the tip circle 14 is indicated by the dimension a. It will be seen clearly from FIG. 15 that, after the inner shell 5 has been pressed in, a hollow space 24 remains between two tooth flanks, which hollow space 24 has to be of a sufficiently large dimension to ensure that the material of the inner shell displaced by the teeth can escape.

Figure 15:
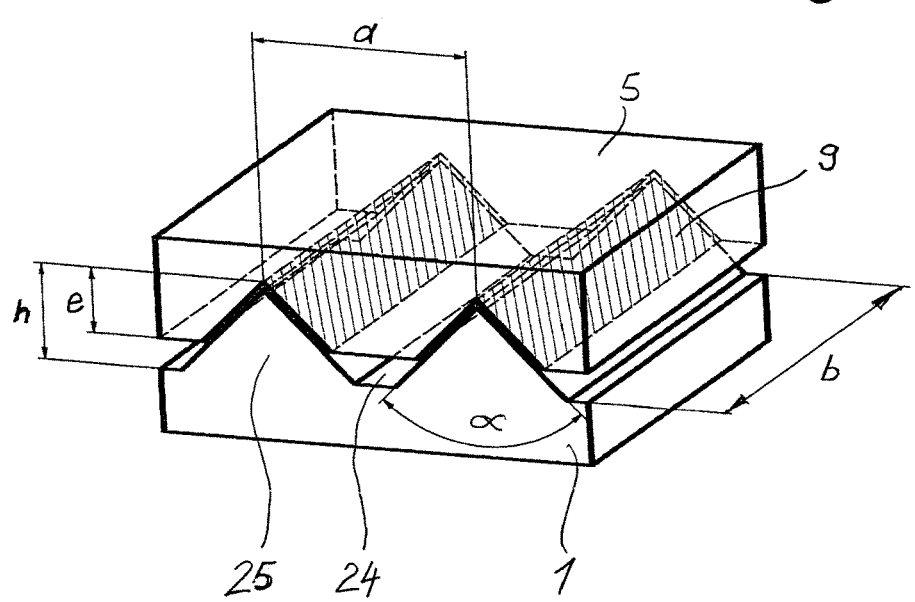
FIG. 15 shows a perspective and schematic view of the engagement of two teeth of a toothing system into the material of the inner shell.

The main parameters of the toothing system are shown schematically again in FIG. 15. The penetration depth e should not exceed 0.1 mm to 1 mm. It is desirable to have the largest possible number of teeth 25 at a uniform distance a from each other. These teeth have a height h, wherein a difference remains between e and h, such that a hollow space 24 remains between adjacent tooth flanks 9. b is the width of the toothing system or, more precisely, the width of the penetration of the individual teeth into the material of the inner shell 5. As mentioned at the outset, the transmissible torque increases the greater the width b of the toothing system, at a given penetration depth e. By contrast, the pressing-in force is determined substantially by the penetration depth e. The required dimensions of the toothing system are determined, for different shell sizes, on the basis of a torque predefined by medical standards, e.g. a torque of greater than 12 Nm, that the inner shell has to be able to transmit to the outer shell.

The invention claimed is:

1. A joint socket implant, comprising:
   an outer shell with a convex outer face and a concave inner face, which has a toothing system in a circular circumferential region,
   wherein flanks of the toothing system are oriented parallel to a longitudinal central axis of the outer shell,
   a tooth profile has a tooth height defined as the difference between a radius of a tip circle and a radius of a root circle of the toothing system,
   an inner shell inserted into the outer shell,
   a hardness of the outer shell is greater than that of the inner shell,
   the region of the inner shell coming into contact with the toothing system has a size, relative to the tip circle of the toothing system, such that an inhibition of the rotatability of the two shells, relative to each other, is achievable by the material of the inner shell being displaced by the toothing system,
   wherein a hollow space remains between the flanks of adjacent teeth and the inner shell inserted into the toothing system.

2. The joint socket implant as claimed in claim 1, wherein the outer shell is produced from titanium or from a titanium-based, steel-based, cobalt-based or zirconium-based alloy.

3. The joint socket implant as claimed in claim 1, wherein the inner shell is produced from a polyethylene.

4. The joint socket implant as claimed in claim 3, wherein the polyethylene is one of polyethylene of ultra-high molecular weight (UHMWPE), highly crosslinked polyethylene (HCPE), polyetheretherketone (PEEK) or polyaryletherketone (PAEK).

5. The joint socket implant as claimed in claim 1, wherein the toothing system extends continuously about the circular circumferential region.

6. The joint socket implant as claimed in claim 1, wherein the outer shell and the inner shell have corresponding axial locking elements via which they are locked onto each other relative to the common longitudinal central axis.

7. The joint socket implant as claimed in claim 6, wherein the circumferential region with the toothing system is arranged in a cylindrical portion of the concave inner face of the outer shell adjacent to the corresponding locking elements, relative to the common longitudinal central axis.

8. The joint socket implant as claimed in claim 1, wherein the toothing system penetrates into the material of the inner shell with a tooth penetration depth of between 0.1 and 1.0 mm.

9. The joint socket implant as claimed in claim 8, wherein the total number of teeth of the toothing system and a width of the teeth, relative to the longitudinal central axis, are chosen in such a way that inhibition of the rotatability exceeds a predefined setpoint torque.

10. The joint socket implant as claimed in claim 1, wherein the individual teeth of the toothing system enclose an angle of 45° to 100°.

11. The joint socket implant as claimed in claim 9, wherein side flanks of the teeth are planar surfaces.

12. The joint socket implant as claimed in claim 1, wherein the toothing system extends only partially about the circular circumferential region.

13. The joint socket implant as claimed in claim 1, wherein the circumferential region with the toothing system, relative to the central longitudinal axis, lies closer to an equator of the outer shell than to a pole.

14. The joint socket implant as claimed in claim 1, wherein the inner shell is made of a plastic material with a Shore hardness (D) of between 50 and 85.

15. The joint socket implant as claimed in claim 1, wherein the toothing system is capable of transmitting a torque greater than 10 Nm.

* * * * *